United States Patent [19]

Gibbon

[11] Patent Number: 5,094,238
[45] Date of Patent: Mar. 10, 1992

[54] MOLDABLE BODY PAD

[75] Inventor: Robert M. Gibbon, Fort Worth, Tex.

[73] Assignee: JMK International, Inc., Fort Worth, Tex.

[21] Appl. No.: 614,297

[22] Filed: Nov. 16, 1990

[51] Int. Cl.$^5$ .............................................. A61F 7/08
[52] U.S. Cl. .................................. 128/403; 128/402; 219/10.55 M
[58] Field of Search ............... 128/399, 402, 403, 379, 128/380, 155, 156; 126/204, 207, 263; 62/259.3; 383/901; 165/46; 219/10.55 M, 10.55 F, 10.55 E, 10.55 R, 10.55 D; 604/368

[56] References Cited

U.S. PATENT DOCUMENTS

| | | | |
|---|---|---|---|
| 2,595,328 | 5/1952 | Bowen | 128/403 |
| 4,046,983 | 9/1977 | Ishino et al. | 219/10.55 D |
| 4,576,169 | 3/1986 | Williams | 128/402 |
| 4,596,250 | 6/1986 | Beisang | 128/402 |
| 4,671,267 | 6/1987 | Stout | 128/402 |
| 4,756,311 | 7/1988 | Francis, Jr. | 128/403 |
| 4,832,031 | 5/1989 | Last | 128/403 |
| 4,914,717 | 4/1990 | Gibbon | 128/399 |
| 4,920,964 | 5/1990 | Francis, Jr. | 128/403 |

Primary Examiner—William H. Grieb
Assistant Examiner—Mark S. Graham
Attorney, Agent, or Firm—Charles D. Gunter, Jr.

[57] ABSTRACT

A method is shown for applying heat to a localized area such as a joint of the human body. A malleable heating pad is provided which can be applied to the localized area by molding the heating pad about the localized area. The heating pad includes a layer of uncured, microwaveable rubber formed from a rubber matrix having blended therein an electromagnetic absorptive material. The heating pad is heated to a temperature above ambient by exposing the heating pad to microwave energy and the pad is then applied to the affected area by molding the pad about the localized area.

7 Claims, 1 Drawing Sheet

MOLDABLE BODY PAD

BACKGROUND OF THE INVENTION

1. Field of the Invention

The present invention relates generally to therapeutic devices for the treatment of localized injury or pain and specifically, to a microwave actuable heating pad which is malleable allowing the pad to molded about the localized area to be treated.

2. Description of the Prior Art

It is well known that, for a therapeutic effect, both human and animal muscle tissue should be heated in some circumstances and chilled in others. For instance, sprained or strained muscle tissues are generally chilled to reduce swelling and further damage. Small, specialized ice packs are known which are designed for application of cold to localized areas.

Similarly, a variety of devices are known in the prior art for applying heat to localized areas of pain. Such devices include hot water bottles, which are ordinarily made of flexible rubber, and which can also include insulated coverings for conserving heat when the hot water bottle is filled with hot water. For instance, see U.S. Pat. No. 2,072,564, issued Mar. 2, 1937, to May, entitled *Hot Water Bottle Cover*. Other heating devices include electric heating pads in which a plurality of resistive heating elements are electrically actuated to provide a source of heat for treating localized area of pain.

The prior art hot water bottle suffers from a variety of disadvantages. The device is cumbersome to use since it is necessary to fill the interior of the bottle with hot water from a tap. Even with an insulated covering, the device lacks the ability to retain a significant amount of heat for a prolonged period of time. The electric heating pad, while more efficient in operation and heat transfer ability, suffers from various limitations including the encumbrance which results from being attached to a power source by wires. Also, the electric pad can constitute a hazard from electrical voltage if used around water, such as in a bath area.

Another shortcoming of the prior art devices is that the heating device is not generally putty-like in nature and cannot be effectively molded about the body part to be treated, for instance the elbow or the knee area of the human body. U.S. Pat. Nos. 4,756,311 and 4,920,964 are related patents which both show thermal compresses which contain a cold pack gel material. The gel material is laminated by an envelope made of a film of synthetic resin. The gel pack is microwaved in order to actuate and heat the gel material but the sealed envelope is not moldable about a body part to the extent that a putty-like compound would be. U.S. Pat. No. 4,671,267 shows a body of gel which is encased within a heat permeable stretch fabric and applied to a body part. The reference also teaches applying the gel material directly to the injured skin to create a temporary skin with improved air permeability. The patent does not teach the inclusion of an electromagnetic absorptive agent to render the material microwaveable, however.

A need exists for an improved device and method for applying heat to localized areas of both human and animal bodies for relief of pain and for the prevention and/or treatment of injury.

A need also exists for such a device which is heat actuable without the presence of electric wires and which retains its heat transfer properties for a prolonged time period.

A need also exists for such a device which is putty-like in nature, allowing the device to be molded about the localized area to be treated in order to improve the therapeutic effect thereof.

SUMMARY OF THE INVENTION

In the method of the invention, a malleable heating pad is applied to a localized area of a body by molding the heating pad about the localized area. The heating pad is formed from at least one layer of an uncured, microwaveable rubber comprising a rubber matrix having blended therein an electromagnetic absorptive material. The heating pad is heated to a temperature above ambient by exposing the heating pad to microwave energy prior to application to the localized area. The heating pad is then applied to the body by molding the heating pad about the localized area.

Preferably, the uncured, microwaveable rubber is a silicone rubber formulated from a polyorganosiloxane gum and an electromagnetic absorptive material, the rubber being further characterized by the absence of a catalyst, thereby rendering the rubber non-curing. The electromagnetic absorptive material can be conveniently selected from the group consisting of ferrites, powdered iron, powdered aluminum and zinc oxide.

The heating pad is preferably covered with a covering formed of a material which is non-absorptive of microwave energy. This covering can comprise a pouch having opposing pockets, one of the opposing pockets containing the microwaveable silicone rubber layer. The opposing pocket can contain a sponge-like material. To apply wet heat to the localized area being treated, the sponge can be wet and the covering folded to make the silicone rubber be the outer layer. To apply dry heat, the covering is folded to make the microwaveable silicone rubber be the inner layer, the dry sponge being folded over the inner layer to serve as an insulating outer layer.

Additional objects, features and advantages will be apparent in the written description which follows.

BRIEF DESCRIPTION OF THE DRAWINGS

in FIG. 1;

DETAILED DESCRIPTION OF THE INVENTION

Figure 1:
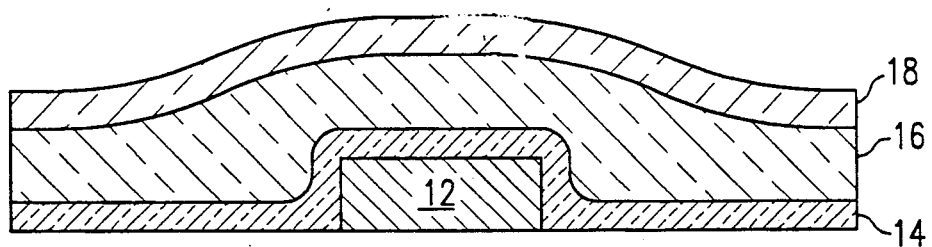
FIG. 1 is a plan view of the moldable heating pad of the invention showing the heating pad installed within a cloth covering.
Figure 2:
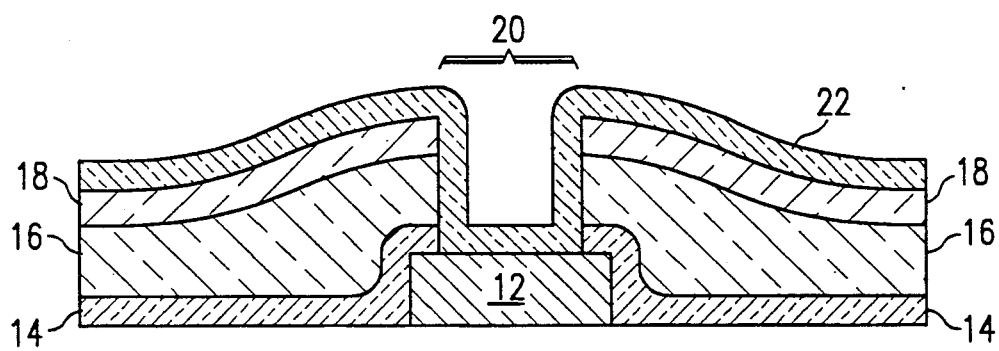
FIG. 2 is a cross-sectional view taken along lines II.—II.

Turning to FIG. 1 there is shown a moldable heating pad of the invention designated generally as 10. The heating pad 10 includes at least one layer 11 of a matrix material having blended therein an electromagnetic absorptive material to produce a homogeneous matrix composition which is heatable by exposure to microwave energy. The matrix material can comprise any of a number of commercially available flexible, elastomeric materials for instance, the matrix material could be formed from a natural rubber, a synthetic rubber, a styrene butadiene rubber, ethylene propylene rubber, chloroprene, nitrile rubber or a silicone rubber. The criteria for selecting a candidate material are its ability to be heat actuated by exposure to electromagnetic energy, its heat stability, its ability to be easily compounded or blended with an electromagnetic absorptive material and its malleable nature, allowing it to be molded about the localized area to be treated. The preferred material is an uncured silicone rubber because of its heat stability and its superior resistance to embrittlement due to oxidation, ozone attack and general use.

The preferred matrix material for the microwaveable layer 11 can be manufacture by blending together a polyorganosiloxane gum with a particulate electromagnetic absorptive material to produce a homogeneous silicone rubber composition which is uncured, putty-like in nature and heatable by exposure to microwave energy. The organopolysiloxane polymers or gums employed in the preferred matrices of the invention are well known material that can be made by standard methods known in the art. The preferred polymer is an organopolysiloxane gum which contains methyl, vinyl, phenyl and/or 3,3,3-trifluoropropyl radicals attached to the silicone atoms of the polymeric siloxane. Examples of organopolysiloxane gums are those polymers, copolymers and mixtures thereof wherein the siloxy units can be dimethylsiloxane, phenylmethylsiloxane, 3,3,3-trifluoropropylmethylsiloxane, diphenylsiloxane, methylvinylsiloxane, and phenylvinylsiloxane. A discussion of the preparation of such organic compounds can be found, for example, in: Eaborn, D, *Organosilicone Compounds,* Academic Press, New York, 1959; Montermoso, J. C., *Silicone Rubbers,* Morton, E. D., *Introduction To Rubber Technology,* Reinhold Publishing Corp., New York, 1959; and Rochow, E. G., *An Introduction To The Chemistry of Silicones,* to Ed. John Wiley and Sons, New York, 1951.

In order to provide a matrix composition which is microwave heatable, a particulate, electromagnetic absorptive material is blended with the matrix material. A number of such materials are commercially available, including ferrites, powdered iron, powdered aluminum, and zinc oxide. Preferred materials include zinc oxide and powdered aluminum when blended in the range from about 5 to 30 parts per 100 parts polyorganosiloxane gum, thereby producing a silicone rubber blend which is heatable in the range from about 160°-180° F. by exposure to a 700 watt microwave oven for one to five minutes The matrix composition should require on the order of 40-50 minutes to return to 60° F.

The organopolysiloxane gum can contain any of the conventional filler materials. These filler materials are well known in the art and are commercially available from a number of sources. The preferred material is a silica filler, sometimes referred to as a reinforcing filler, or a mixture of silica filler and an extending filler. Examples of silica filler which can be utilized to reinforce the organopolysiloxane elastomer are fumed silica, precipitated silica, silica aerogel, etc. The filler material, including reinforcing and non-reinforcing fillers, is preferably used in the range of about 10-260 parts of filler per 100 parts of organopolysiloxane gum or elastomer, most preferably in the range from about 20-80 parts of filler.

The microwaveable rubber composition is further characterized by the absence of a catalyst, thereby rendering the rubber non-curing. Because of its uncured, putty-like nature, the malleable heating pad can be applied to the localized area of the body being treated by molding the heating pad about the localized area.

In addition to the above described ingredients, the rubber matrix compositions which are preferred in the invention can contain heat stability additives, compression set additives, additives to improve handling properties, dyes or coloring additives and other additives conventionally used in heat cured silicone elastomers and also room temperature cure elastomers.

The preferred microwaveable silicone rubber matrix is made by blending or milling together the various constituents. The order of adding the elastomer, filler and electromagnetic absorptive material is not critical. The following example is intended to be illustrative of the invention:

| | |
|---|---|
| 40 Duro silicone Base* | 100 parts |
| Vinyl dimethyl end-stopped dimethyl polysiloxane polymer | 50 parts |
| Aluminum powder | 10 parts |

*Siloxane polymer with added filler, either fumed silica or precipitated silica such as Hi-Sil 233.

As shown in FIG. 1, the microwave actuable layer 11 is preferably contained within a covering 13 which is formed of a material which is non-absorptive of microwave energy, for instance cloth. The preferred cloth covering shown in FIG. 1 can conveniently be provided as a pouch which includes opposing pockets 15, 17, one of the pockets 17 containing the layer of uncured, microwaveable silicone rubber and the opposite pocket 15 containing an open cell sponge 19. The opposing pockets 15, 17 are joined by a center strip or hinge 21, thereby allowing the pockets to be folded one upon the other along the center strip 21. Pocket 15 has top and bottom edges 23, 25 and opposing side edges 27, 29. Pocket 17 has top and bottom edges 31, 33 and opposing side edges 35, 37. The microwaveable layer 11 and sponge 19 can be enclosed within their respective pockets as by suitable stitching 39.

Figure 3:
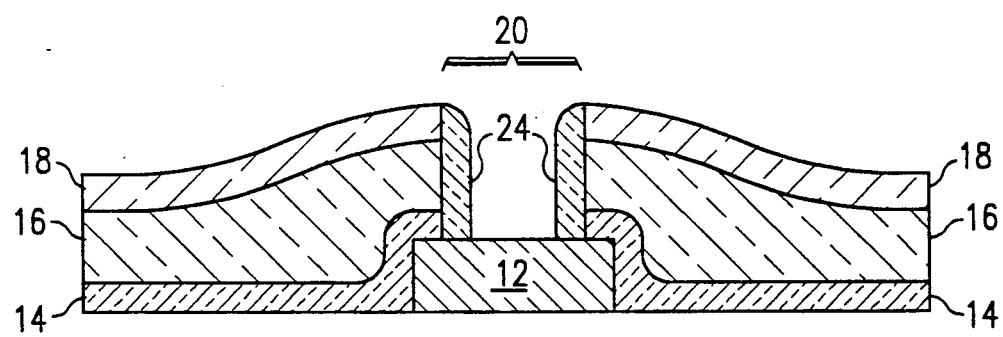
FIG. 3 is a side, elevational view of the cloth covered heating pad of the invention wrapped about the knee joint to apply dry heat to the knee of the user.

In use, the moldable heating pad 11 of the invention can be used to provide either wet or dry heat to an affected area. FIG. 3 shows the device of the invention installed on the knee of a user with the covering folded along the center strip 21 so that the open cell sponge 19 overlays the microwaveable layer 11. In this way, the microwaveable layer, having previously been exposed to microwave energy in an oven, can be used to apply dry heat to the affected joint The dry, open cell sponge 19 provides an insulating layer to retain the dry heat on the affected area.

Figure 4:
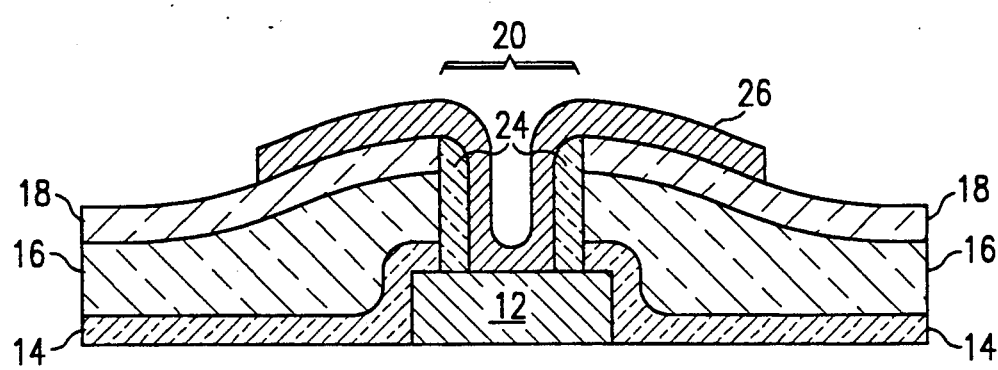
FIG. 4 is a similar elevational view of a cloth covered heating pad of the invention wrapped about the knee joint to apply wet heat to the knee of the user.
Figure 1:
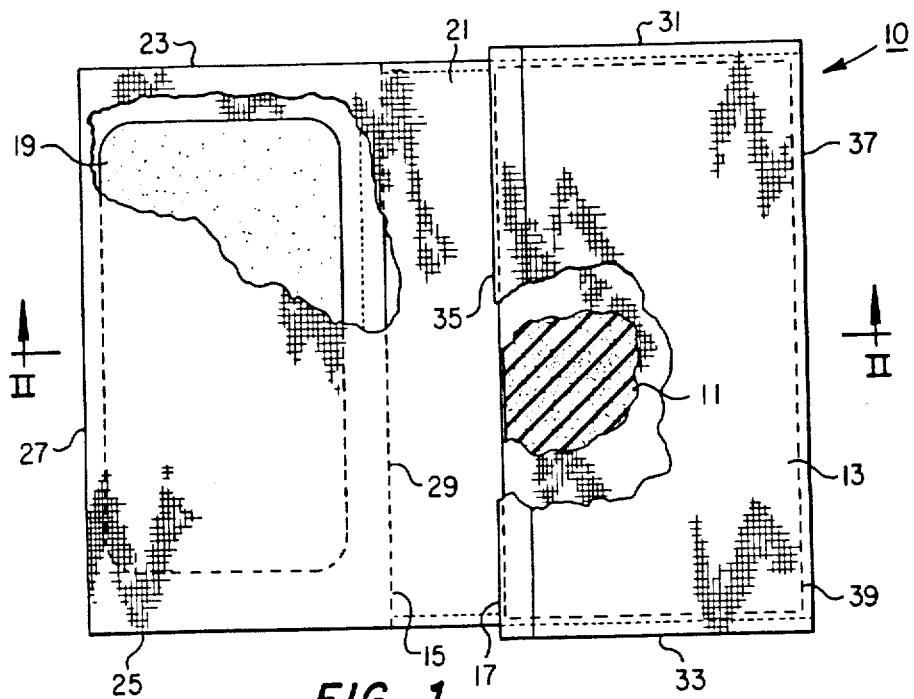
Figure 2:
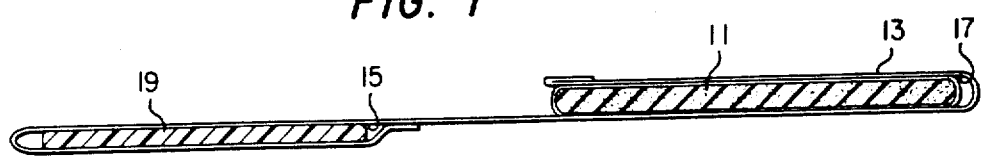
Figures 3, 4:
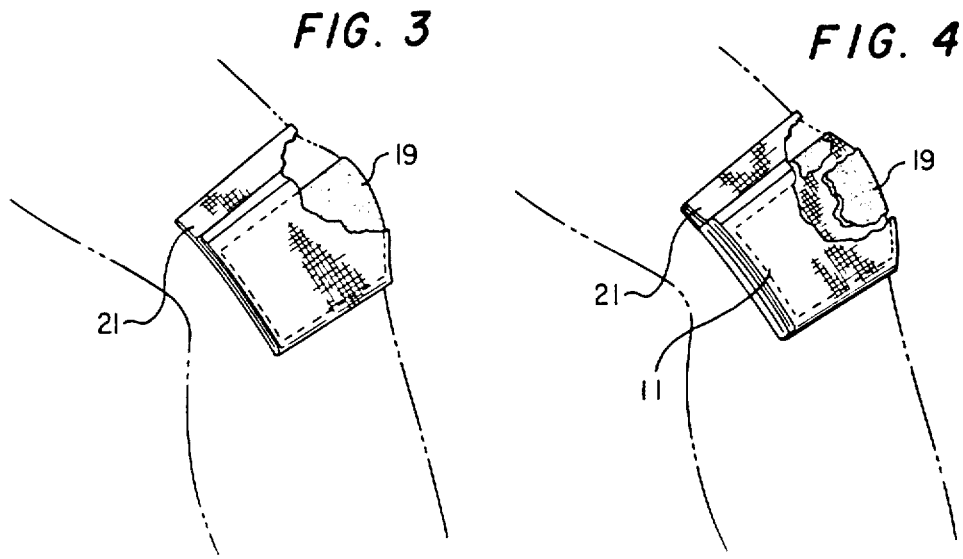

FIG. 4 shows the device of the invention folded along the center strip 21 in the opposite manner so that the open cell sponge layer 19 contacts the joint and so that the microwaveable layer 11 overlays the sponge layer. By exposing the microwaveable layer 11 to microwave energy and by wetting the sponge layer 19, the device can be used to apply wet heat to the affected joint. The microwaveable outer layer 11 acts through the wet, inner sponge layer 19 to apply wet heat.

The primary use for the heating pad of the invention would be as a therapeutic device for relieving joint pain in the human body. As will be easily understood, the device can also be applied to the joints of animals as well. Any localized area can be treated, such as the knee, ankle or elbow joints. The pad is heated in a microwave oven to the appropriate operating temperature. For instance, using a 700 watt microwave oven at 100% power for three minutes, a ⅜ inch thick pad reaches a preferred operating temperature of approximately 170° F. It then takes the pad approximately 45 minutes to return to 60° F.

An invention has been provided with several advantages. The heating pad of the invention can be used for a variety of medical applications without the encumbrance of being attached to a power source by wires. Also, the pad of the invention does not represent a hazard from the electric source, even if water is present. Because of its malleable nature, the pad can be molded about the localized area, thereby speeding relief and providing more effective treatment to the source of pain or injury. The pad is simple and economical to manufacture and is not easily damaged in use.

While the invention has been shown in only one of its forms, it is not thus limited but is susceptible to various changes and modifications without departing from the spirit thereof.

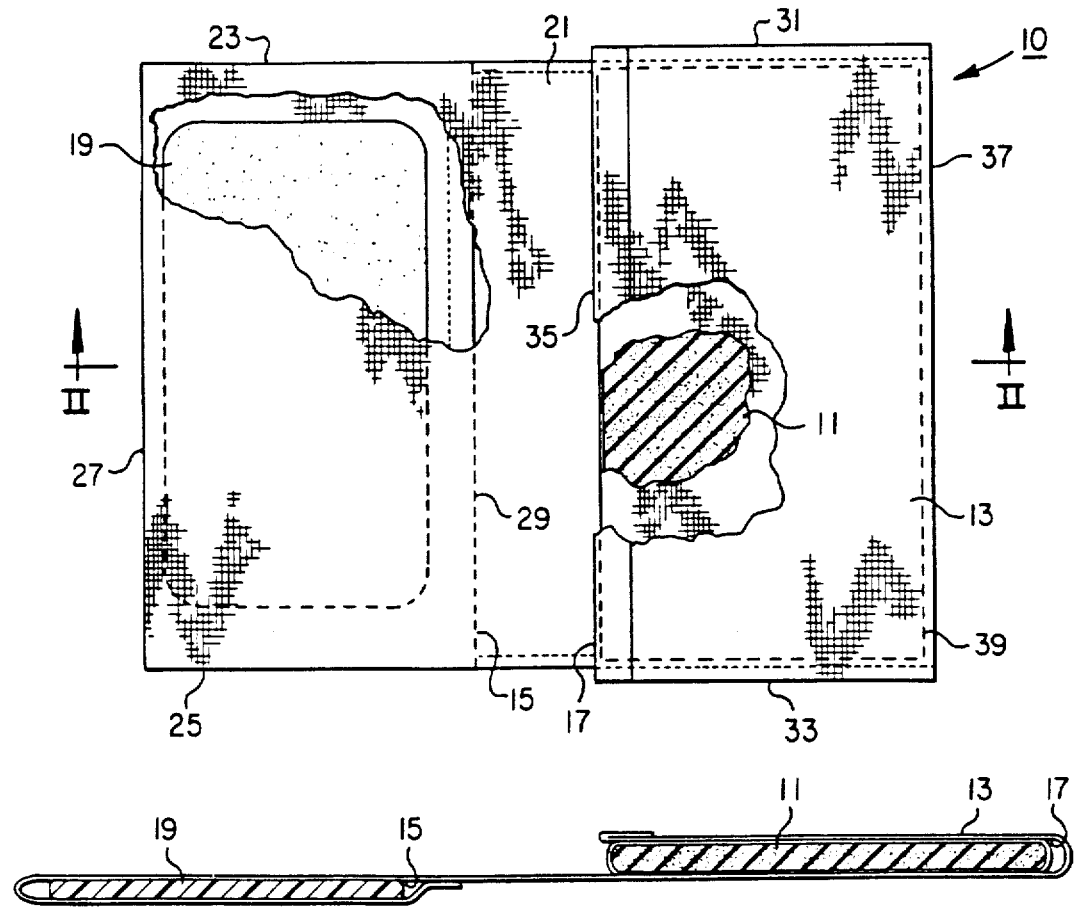

I claim:

1. A method of applying heat to a localized area of a body, the method comprising the steps of:

providing a malleable heating pad which can be applied to the localized area by molding the heating pad about the localized area, the heating pad being formed from at least one layer of an uncured, microwaveable rubber comprising a polyorganosiloxane gum having blended therein an electromagnetic absorptive material, the microwaveable rubber being further characterized by the absence of a catalyst, thereby rending the rubber non-curing;

covering the microwaveable silicone rubber layer with a covering formed of a material which is non-absorptive of microwave energy;

heating the heating pad to a temperature above ambient by exposing the heating pad to microwave energy prior to application to the localized area; and applying the heating pad to the body by molding the heating pad about the localized area.

2. The method of claim 1, wherein the electromagnetic absorptive material is selected from the group consisting of ferrites, powdered iron, powdered aluminum and zinc oxide.

3. A moldable heating pad formed of a flexible, elastomeric material for treating a localized area of pain in the human body, the moldable heating pad comprising:

at least one layer of uncured, microwaveable silicone rubber, the uncured, microwaveable silicone rubber being compounded from a polyorganosiloxane gum and an electromagnetic absorptive material selected form the group consisting of ferrites, powdered iron, powdered aluminum and zinc oxide, the electromagnetic absorptive material being blended in the range from about 5 to 30 parts by weight per 100 parts by weight polyorganosiloxane gum to produce a microwaveable silicone rubber which is heatable in the range from about 160° to 180° F. by exposure to a 700 watt microwave oven at full power for about 1 to 5 minutes, the rubber being further characterized by the absence of a catalyst, thereby rendering the rubber non-curing and, wherein the polyorganosiloxane gum further has blended therein from about 10 to 260 parts by weight silica filler per 100 parts by weight polyorganosiloxane gum;

a covering for the uncured, microwaveable silicone rubber, the covering being formed of a material which is non-absorptive of microwave energy.

4. The foldable heating pad of claim 3, wherein the covering comprises a pouch having opposing pockets which are joined at a center strip, one of the pockets containing the uncured, microwaveable silicone rubber and the opposing pocket containing a water absorptive material.

5. The moldable heating pad of claim 4, wherein the water absorptive material is an open cell sponge.

6. A method of treating a localized area of pain in the human body, comprising the steps of:

applying a heating pad to the localized area by molding the heating pad about the localized area, the heating pad comprising at least one layer of uncured, microwaveable silicone rubber which has been heated to a temperature above ambient by exposure to microwave energy prior to application to the localized area, the microwaveable silicone rubber comprising a polyorganosiloxane gum having blended therein an electromagnetic absorptive material;

wherein the microwaveable silicone rubber is contained within a covering formed of a material which is non-absorptive of microwave energy, the covering comprising a pouch having opposing pockets, one of the opposing pockets containing the uncured, microwaveable silicone rubber and the opposing pouch containing an open cell sponge; and wherein the heating pad is applied to the localized area by placing the silicone rubber pocket over the affected area and folding the sponge pocket over the silicone rubber pocket so that the sponge pocket overlays the silicone rubber pocket.

7. A method of treating a localized area of pain in the human body, comprising the steps of:

applying a heating pad to the localized area by molding the heating pad about the localized area, the heating pad comprising at least one layer of uncured, microwaveable silicone rubber which has been heated to a temperature above ambient by exposure to microwave energy prior to application to the localized area, the microwaveable silicone rubber comprising a polyorganosiloxane gum having blended therein an electromagnetic absorptive material;

wherein the microwaveable silicone rubber is contained within a covering formed of a material which is non-absorptive of microwave energy, the covering comprising a pouch having opposing pockets, one of the opposing pockets containing the uncured, microwaveable silicone rubber and the opposing pouch containing an open cell sponge; and wherein the heating pad is applied to the localized area by wetting the sponge and placing the sponge pocket over the affected area, the silicone rubber pocket being folded over the sponge pocket so that the silicone rubber pocket overlays the sponge pocket.

* * * * *

UNITED STATES PATENT AND TRADEMARK OFFICE
CERTIFICATE OF CORRECTION

PATENT NO. : 5,094,238

DATED : March 10, 1992

INVENTOR(S) : Robert M. Gibbon

It is certified that error appears in the above-indentified patent and that said Letters Patent is hereby corrected as shown below:

The title page, should be deleted to be replaced with the attached title page.

The drawing sheet consisting of Figs. 1 - 4 should be deleted to be replaced with the sheet of drawing, consisting of Figs. 1 - 4, as shown on the attached page.

Signed and Sealed this

Twenty-sixth Day of October, 1993

Attest:

BRUCE LEHMAN

Attesting Officer

Commissioner of Patents and Trademarks

United States Patent [19]

Gibbon

[11] Patent Number: 5,094,238
[45] Date of Patent: Mar. 10, 1992

[54] MOLDABLE BODY PAD

[75] Inventor: Robert M. Gibbon, Fort Worth, Tex.

[73] Assignee: JMK International, Inc., Fort Worth, Tex.

[21] Appl. No.: 614,297

[22] Filed: Nov. 16, 1990

[51] Int. Cl.⁵ ............................................. A61F 7/08
[52] U.S. Cl. ................................ 128/403; 128/402; 219/10.55 M
[58] Field of Search ............... 128/399, 402, 403, 379, 128/380, 155, 156; 126/204, 207, 263; 62/259.3; 383/901; 165/46; 219/10.55 M, 10.55 F, 10.55 E, 10.55 R, 10.55 D; 604/368

[56] References Cited

U.S. PATENT DOCUMENTS

| | | | |
|---|---|---|---|
| 2,595,328 | 5/1952 | Bowen | 128/403 |
| 4,046,983 | 9/1977 | Ishino et al. | 219/10.55 D |
| 4,576,169 | 3/1986 | Williams | 128/402 |
| 4,596,250 | 6/1986 | Beisang | 128/402 |
| 4,671,267 | 6/1987 | Stout | 128/402 |
| 4,756,311 | 7/1988 | Francis, Jr. | 128/403 |
| 4,832,031 | 5/1989 | Last | 128/403 |
| 4,914,717 | 4/1990 | Gibbon | 128/399 |
| 4,920,964 | 5/1990 | Francis, Jr. | 128/403 |

Primary Examiner—William H. Grieb
Assistant Examiner—Mark S. Graham
Attorney, Agent, or Firm—Charles D. Gunter, Jr.

[57] ABSTRACT

A method is shown for applying heat to a localized area such as a joint of the human body. A malleable heating pad is provided which can be applied to the localized area by molding the heating pad about the localized area. The heating pad includes a layer of uncured, microwaveable rubber formed from a rubber matrix having blended therein an electromagnetic absorptive material. The heating pad is heated to a temperature above ambient by exposing the heating pad to microwave energy and the pad is then applied to the affected area by molding the pad about the localized area.

7 Claims, 1 Drawing Sheet